(12) United States Patent
Ju et al.

(10) Patent No.: US 9,468,700 B2
(45) Date of Patent: Oct. 18, 2016

(54) WOUND DRESSINGS WITH ENHANCED GAS PERMEATION AND OTHER BENEFICIAL PROPERTIES

(71) Applicant: The University of Akron, Akron, OH (US)

(72) Inventors: Lu-Kwang Ju, Akron, OH (US); Soroosh Dashtbozorg, Akron, OH (US); Napaporn Vongpanish, Akron, OH (US)

(73) Assignee: The University of Akron, Akron, OH (US)

( * ) Notice: Subject to any disclaimer, the term of this patent is extended or adjusted under 35 U.S.C. 154(b) by 0 days.

(21) Appl. No.: 14/372,924

(22) PCT Filed: Jan. 25, 2013

(86) PCT No.: PCT/US2013/023199
§ 371 (c)(1),
(2) Date: Jul. 17, 2014

(87) PCT Pub. No.: WO2013/112875
PCT Pub. Date: Aug. 1, 2013

(65) Prior Publication Data
US 2014/0364381 A1 Dec. 11, 2014

Related U.S. Application Data

(60) Provisional application No. 61/590,452, filed on Jan. 25, 2012.

(51) Int. Cl.
*A61L 15/22* (2006.01)
*A61L 15/24* (2006.01)
*A61L 15/44* (2006.01)
*A61L 15/48* (2006.01)
*A61L 15/60* (2006.01)

(52) U.S. Cl.
CPC ............. *A61L 15/225* (2013.01); *A61L 15/22* (2013.01); *A61L 15/24* (2013.01); *A61L 15/44* (2013.01); *A61L 15/48* (2013.01); *A61L 15/60* (2013.01); *A61L 2300/22* (2013.01); *A61L 2300/404* (2013.01)

(58) Field of Classification Search
None
See application file for complete search history.

(56) References Cited

U.S. PATENT DOCUMENTS

| 4,532,267 A * | 7/1985 | Allan ........................ C08L 5/08 264/1.1 |
| 4,977,892 A * | 12/1990 | Ewall .................... A61F 13/023 523/105 |
| 5,981,497 A | 11/1999 | Maingault |
| 2004/0127836 A1 | 7/2004 | Sigurjonsson et al. |
| 2009/0126948 A1 | 5/2009 | DeSanto |
| 2010/0249273 A1 | 9/2010 | Scales et al. |
| 2013/0039968 A1 | 2/2013 | Messier |

FOREIGN PATENT DOCUMENTS

EP 2093256 A2 8/2009

OTHER PUBLICATIONS

Di Indigo Kinder, blue-green algae, internet article published Apr. 27, 2009, obtained from https://web.archive.org.*
Hom, Bandage Contact Lenses to the Rescue, internet article, http://www.optometricmanagement.com/articleviewer.aspx?articleID=71786, Nov. 1, 2006.*

* cited by examiner

*Primary Examiner* — Layla Berry
(74) *Attorney, Agent, or Firm* — Renner Kenner Greive Bobak Taylor & Weber (57) ABSTRACT

A wound dressing comprises a wound dressing substrate including one or more of gas vesicles, rhamnolipids, and sophorolipids. The wound dressing can be fabric-based or hydrogel-based. Methods for producing a wound dressing are also provided.

11 Claims, 4 Drawing Sheets

WOUND DRESSINGS WITH ENHANCED GAS PERMEATION AND OTHER BENEFICIAL PROPERTIES

CROSS-REFERENCE TO RELATED APPLICATION

This application is a non-provisional of U.S. Patent Provisional Application No. 61/590,452, filed on Jan. 25, 2012, the contents of which are incorporated herein by reference.

FIELD OF THE INVENTION

The present invention generally relates to wound dressings. In some embodiments, the present invention relates to wound dressings with enhanced gas permeation and other beneficial properties and to methods of making.

BACKGROUND OF THE INVENTION

Wound dressings can be used to cover wounds in an effort to assist in the wound healing process. In general, wound dressings can be classified as passive or active types, depending on their roles in wound healing. Passive wound dressings refer to the dressings which only provide a cover for the wound at the basic level, whereas active wound dressings are those facilitating the management of the wound and promoting wound healing.

An ideal wound dressing will possess certain characteristics in order to help with the wound healing process. Examples of desired characteristics include enhanced antimicrobial activities, the ability to retain and absorb moisture, and allowing good permeation of gas, particularly for the supply of oxygen from the ambient air to the covered wound area and for removal of excess carbon dioxide from the wound area to the ambient air.

Thus, a need in the art exists for an improved wound dressing. The current invention provides a wound dressing with enhanced gas permeation and other beneficial properties.

SUMMARY OF THE INVENTION

A first embodiment of this invention provides a wound dressing comprising a wound dressing substrate including gas vesicles, rhamnolipids, and sophorolipids.

A second embodiment provides a wound dressing as in the first embodiment, wherein the wound dressing substrate includes a wound dressing hydrogel.

A third embodiment provides a wound dressing as in either the first embodiment or the second embodiment, wherein the wound dressing hydrogel comprises a polymer selected from the group consisting of polyvinyl alcohol, alginate, chitosan, carboxyethyl chitosan, methylcellulose, gelatin, soy protein, wheat protein, xanthan gum, gum arabic, polyacrylamide, polyalcohols, polysaccharides, polyamines, proteins, or mixtures thereof.

A fourth embodiment provides a wound dressing as in any of the first through third embodiments, wherein the wound dressing substrate includes a wound dressing fabric.

A fifth embodiment provides a wound dressing as in any of the first through fourth embodiments, wherein the wound dressing comprise fabrics formed of fibers selected from the group consisting of cotton, hemp, jute, and flax, rayon, modal, nylon, polyester, polyacrylonitrile, polymethyl methacrylate, polyethylene, polypropylene, acrylics, polyolefins, silk, paraffin tulle, or mixtures thereof.

A sixth embodiment provides a wound dressing as in any of the first through fifth embodiments, wherein the wound dressing substrate includes fibers that are embedded with gas vesicles.

A seventh embodiment provides a wound dressing as in any of the first through sixth embodiments, wherein the wound dressing substrate includes fibers having gas vesicles attached thereto.

An eighth embodiment provides a wound dressing as in any of the first through seventh embodiments, wherein the wound dressing further comprises a barrier layer and a controlled-gas-diffusion layer.

A ninth embodiment provides a wound dressing as in any of the first through eighth embodiments, wherein the wound dressing substrate includes fibers that are embedded with gas vesicles.

A tenth embodiment provides a wound dressing as in any of the first through ninth embodiments, wherein the wound dressing substrate includes fibers having gas vesicles attached thereto.

An eleventh embodiment provides a wound dressing as in any of the first through tenth embodiments, wherein the wound dressing comprises a wound dressing substrate including gas vesicles.

A twelfth embodiment provides a wound dressing as in any of the first through eleventh embodiments, wherein the wound dressing comprises a wound dressing substrate including rhamnolipids.

A thirteenth embodiment provides a wound dressing as in any of the first through twelfth embodiments, wherein the wound dressing comprises a wound dressing substrate including sophorolipids.

A fourteenth embodiment provides a method for producing a wound dressing, the method comprising the steps of preparing a plurality of fibers, preparing a fabric wound dressing substrate from the plurality of fibers, and incorporating one or more of gas vesicles, rhamnolipids, and sophorolipids in the fabric wound dressing substrate.

A fifteenth embodiment provides a method as in the fourteenth embodiment, wherein, in said steps of preparing, said fibers include gas vesicles embedded in or incorporated on or both embedded in and incorporated on the plurality of fiber, such that the gas vesicles are incorporated into the fabric wound dressing substrate upon said step of preparing.

A sixteenth embodiment provides a method as in either the fourteenth embodiment or the fifteenth embodiment, wherein said step of incorporating occurs after said step of preparing a fabric wound dressing and includes placing the fabric wound dressing substrate in a solution comprising one or more of gas vesicles, rhamnolipids, and sophorolipids such that the one or more of gas vesicles, rhamnolipids, and sophorolipids are absorbed into the fabric wound dressing.

A seventeenth embodiment provides a method for producing a wound dressing, the method comprising the steps of preparing a hydrogel polymer solution comprising a hydrogel polymer, crosslinking the hydrogel polymer to form a hydrogel wound dressing substrate, and incorporating one or more of gas vesicles, rhamnolipids, and sophorolipids in the hydrogel wound dressing substrate.

An eighteenth embodiment provides a method as in the seventeenth embodiment, wherein the hydrogel polymer solution includes one or more of gas vesicles, rhamnolipids, and sophorolipids such that the one or more of gas vesicles, rhamnolipids and sophorolipids are incorporated into the wound dressing substrate upon crosslinking of the hydrogel polymer.

A nineteenth embodiment provides a method as in either the seventeenth embodiment or the eighteenth embodiment, wherein the method further comprises at least partially drying the hydrogel wound dressing substrate and wherein said step of incorporating includes placing the at least partially dried hydrogel wound dressing substrate in a solution comprising one or more of gas vesicles, rhamnolipids, and sophorolipids such that the one or more of gas vesicles, rhamnolipids, and sophorolipids are absorbed into the hydrogel wound dressing substrate.

BRIEF DESCRIPTION OF THE DRAWINGS

Advantages of the present invention will become better understood with regard to the following description, appended claims, and accompanying drawings wherein:

DETAILED DESCRIPTION OF ILLUSTRATIVE EMBODIMENTS

The present invention provides wound dressings with improved gas transfer or antimicrobial or moisturizing properties or combinations thereof by incorporating one or more of gas vesicles, rhamnolipids, and sophorolipids into wound dressing substrates such as dressing fabrics and hydrogels. In other embodiments, one or more of gas vesicles, rhamnolipids, and sophorolipids can be incorporated into other wound dressing forms such as solid films, porous foams (e.g., those made of polyurethane or other polymers), porous membranes, creams, meshes, and gauzes.

The wound dressing substrate may be selected from wound dressing hydrogels and wound dressing fabrics. These are each generally known in the art, and, as used herein, the term "wound dressing" as modifying "hydrogels" and "fabrics" is to be understood as connoting that the hydrogels and fabrics are suitable for dressing a wound.

A hydrogel is formed by creating a cross-linked network of polymer chains. The polymer used to form a hydrogel that is used to form a wound dressing of the present invention can be virtually any "hydrogel polymer", which is to be understood herein as any natural or synthetic polymer suitable for making a wound dressing hydrogel. Specific examples of polymers that can be used include polyvinyl alcohol, alginate, chitosan, carboxyethyl chitosan, methylcellulose, gelatin, soy protein, wheat protein, xanthan gum, gum arabic, polyacrylamide, and other polyalcohols, polysaccharides, polyamines, proteins, or mixtures thereof.

In some embodiments, the wound dressing hydrogel is formed of combinations of two or more polymers such as alginate-gelatin, alginate-chitosan, alginate-methylcellulose, alginate-polyethylene glycol, and soy protein-chitosan, While wound dressing hydrogels beneficially retain and absorb moisture, gas transfer through the hydrogel is slow, and in some embodiments of this invention, gas vesicles are incorporated into wound dressing hydrogels to increase their gas transfer rates, thus facilitating the transfer of beneficial gases to the wound bed. Wound dressing hydrogels will also benefit from improved moisturizing of the skin and from the provision of antimicrobial and antifouling properties, and in some embodiments, rhamnolipids and sophorolipids are incorporated into the wound dressing hydrogels to provide these properties. One or more of gas vesicles, rhamnolipids, or sophorolipids can be distributed directly into the hydrogel of the hydrogel-based wound dressings. In other embodiments, gas vesicles can be incorporated into or onto fibers that are dispersed in the hydrogel.

Wound dressing fabrics are generally known and are generally woven or non-woven fabrics formed of woven or non-woven natural or synthetic fibers. The wound dressing fabrics employed in this invention may be virtually any fabric known or later discovered as being suitable for making a wound dressing. Specific examples of fabrics include those woven or non-woven fabrics formed of fibers selected from vegetable fibers such as cotton, hemp, jute, and flax; and synthetic fibers such as cellulose-derived synthetic fibers (e.g., rayon, modal) and polymer-based fibers such as nylon, polyester, polyacrylonitrile, polymethyl methacrylate, polyethylene, polypropylene, and other acrylics and polyolefins.

In some embodiments, the wound dressing fabric is a gauze-type fabric formed of cotton, silk, paraffin tulle, nylon, polyester, polyethylene, or mixtures thereof. In other embodiments, electrospun nanofibers such as those of gelatin and carboxyethyl chitosan-polyvinyl alcohol mixture can be mixed with the other thicker fibers in a wound dressing gauze-type fabric.

While wound dressing fabrics beneficially have increased air space and offer a better internal structure for the wound dressing, the antimicrobial activity and moisture retention of a wound dressing fabric are generally low, and in some embodiments of this invention, rhamnolipids or sophorolipids are incorporated into wound dressing fabrics to increase their antimicrobial and moisturizing activity, thus facilitating improved wound healing. While wound dressing fabrics generally provide good gas transfer, they can benefit from the use of gas vesicles. Using gas vesicles within a wound dressing fabric allows for the loading of a specific gas into the gas vesicles. Also, the gas transfer through a wound dressing fabric will decrease when the fabric absorbs water and exudates from the wound. Having gas vesicles within the wound dressing fabric will help to increase the gas transfer rate. One or more of gas vesicles, rhamnolipids, or sophorolipids can be embedded into the fibers of the fibrous wound dressings.

In one embodiment of the present invention, the wound dressing contains gas vesicles. Gas vesicles are protein-walled hollow structures present in cyanobacteria and halotolerant microorganisms. The gas vesicles are biological and are essentially a gas bubble surrounded by a protein skin. These biologics are essentially non-toxic, both acutely and chronically. Gas vesicles can be randomly distributed throughout a wound dressing hydrogel, distributed in a layer or an area of a multilayered wound dressing, embedded in or attached on prepared fibers that are distributed in a wound dressing hydrogel, or embedded within or attached onto the prepared fibers of a wound dressing fabric.

Gas vesicles are the gas-filled structures making up the gas vacuoles in some planktonic organisms. The shape of a gas vesicle can be a cylindrical tube with conical ends or substantially spherical. In the present invention, the gas vesicles are either obtained or produced and modified. The gas vesicles are hollow with thin vesicle walls consisting of uniquely aligned proteins. The thin walls provide significant strength but do not cause appreciable resistance to gas permeation.

The protein-based walls of the gas vesicles are permeable to gases and can withstand hydrostatic pressure up to the critical pressure before collapsing irreversibly. The inner surface of the gas vesicle wall is hydrophobic, which prevents water from entering the inner gas-filled space. On the other hand, the outer surface is hydrophilic.

Due to their hydrophilic nature, gas vesicles can be dispersed in a wound dressing hydrogel to serve as gas-filled structures in the hydrogel matrix. Gas vesicles can be directly incorporated into the hydrogel. In some embodiments, the wound dressing hydrogel contains randomly distributed individual gas vesicles. In other embodiments, the wound dressing hydrogel contains randomly distributed gas vesicle aggregates. In yet other embodiments, the hydrogel contains both randomly distributed individual gas vesicles and gas vesicle aggregates. Methods of incorporation will be disclosed herein below.

Because the walls of the gas vesicle offer good gas permeation, the use of gas vesicles in a wound dressing hydrogel improves the gas transfer rate through the wound dressing. Gas attempting to pass through a hydrogel without gas vesicles must diffuse through the retained water of the hydrogel, resulting in slow gas transfer. The use of gas vesicles in a wound dressing hydrogel essentially provides the gas a pathway through the hydrogel. The gas has a pathway because the walls of the vesicles allow gas to transfer therethrough. Once inside the gas vesicle, the transfer is quite rapid, as the gas vesicle is simply a hollow structure, as already noted. Therefore, the gas will move through the hydrogel by passing through the gas vesicles, allowing the gas to move from the gas loading surface to the wound surface more quickly.

In some embodiments, gas vesicles are embedded into a fiber and the gas-vesicle-embedded fiber is used to create a wound dressing. In these embodiments, the gas vesicles are added to a solution that is added to the fiber-producing apparatus. Therein, the gas-vesicle-containing solution is fed into a needle or syringe where it will be extruded from a tip. Where electrospinning is utilized, the extrusion occurs by applying a charge to the needle or syringe, which results in the extrusion of a gas-vesicle-containing fiber from the solution onto a nearby grounded plate. Where a pulling method is utilized, a small amount of the mixture will solidify at the tip of the needle and the solidified mixture will then be slowly pulled as it is pumped out of the needle tip. The pulled mixture will then form into a gas-vesicle-containing fiber. These methods of electrospinning and pulling, as well as other related methods such as gas jet, are well known in the art. Methods of incorporating gas vesicles into a fiber will be further disclosed herein below.

In other embodiments, gas vesicles can be bound or attached to the surface of a fiber. In some embodiments, the fibers can be hydrogel-based. In one embodiment, the fibers are used to make a wound dressing fabric. In another embodiment, the fibers are put into a wound dressing hydrogel.

In one embodiment, a wound dressing combines previously discussed embodiments to form a wound dressing hydrogel that contains fibers. These embodiments include all alternatives as discussed above. For instance, one embodiment of the present invention is a wound dressing hydrogel containing one or more of gas vesicles, rhamnolipids, and sophorolipids while also containing fibers. In another embodiment, the wound dressing hydrogel contains one or more of gas vesicles, rhamnolipids, and sophorolipids while also containing fibers that are embedded with gas vesicles.

In one embodiment, the gas vesicles are filled with air as in the ambient atmosphere. In other embodiments, the gas vesicles can be loaded with a gas other than ambient air. In still other embodiments, the gas vesicles will contain the loaded gas and ambient air due to the air from the ambient atmosphere transferring into gas vesicles that are loaded with a gas other than ambient air. In other embodiments, the gas vesicles that are loaded with a gas other than ambient air do not transfer ambient air therein due to a blocking layer between the gas vesicles and the ambient surface.

Two examples of gases that can be used within the gas vesicles include oxygen and nitric oxide. The use of oxygen is desired because one of the limiting factors to wound healing is insufficient oxygen at the wound site. Lack of oxygen causes limitation of cell regeneration that affects the vascularization and healing rate. Incorporating gas vesicles containing oxygen in a wound dressing increases oxygen diffusion rates, enhances the oxygen supply in the biological system (cell culture), and therefore facilitates effective oxygen permeation for wound healing.

The ability to obtain and modify gas vesicles is taught by U.S. Pat. Nos. 6,036,940, 6,413,763, and 7,022,509, which are incorporated herein by reference.

The oxygen carrying capacity of gas vesicles is much higher than current perfluorochemicals used to increase oxygen supply. Using gas vesicles in a wound dressing enhances the oxygen transfer rate and provides more oxygen for cell regeneration.

The gas vesicles improve the gas transfer rate of any gas through the wound dressing. Another gas that can be supplied or controllably released using gas vesicles within a wound dressing is nitric oxide. Nitric oxide (NO) is an important anti-infection gas for wound healing and other medical applications.

Another advantage of gas vesicles is that they have no apparent negative effects on animal cell growth.

Generally, wound dressing hydrogels in accordance with this invention can contain any amount of gas vesicles so long as the loading of the hydrogel with the gas vesicles is not so large as to compromise the hydrogel structure. In some embodiments, particularly those embodiments for enhancing gas permeation, the wound dressing includes from 13 g or more to 150 g or less gas vesicles per kg hydrogel. In some embodiments, the density of gas vesicles is about 0.12 g/cm$^3$. In other embodiments, the density of gas vesicles is in a range from 0.10 g/cm$^3$ or more to 0.14 g/cm$^3$ or less.

In other embodiments, where a volume percentage basis is preferred, the wound dressing includes gas vesicles in a gas vesicle volume-percentage range of 10% or more to 60% or less. In other words, gas vesicles, with the hollow space inside, would occupy approximately from 10% or more to 60% or less of the total hydrogel volume. In other embodiments, particularly those embodiments for enhancing gas permeation, the wound dressing includes from 29 g or more to 105 g or less gas vesicles per kg hydrogel. In other embodiments, where a volume percentage basis is preferred, the wound dressing includes gas vesicles in a gas vesicle volume-percentage range of 20% or more to 50% or less. In yet other embodiments, particularly those embodiments for enhancing gas permeation, the wound dressing includes from 48 g or more to 73 g or less gas vesicles per kg hydrogel. In other embodiments, where a volume percentage basis is preferred, the wound dressing includes gas vesicles in a gas vesicle volume-percentage range of 30% or more to 40% or less.

In some embodiments, particularly those embodiments for nitric oxide release, the wound dressing includes from 0.6 g or more to 48 g or less gas vesicles per kg hydrogel. In other embodiments, where a volume percentage basis is preferred, the wound dressing includes gas vesicles in a gas vesicle volume-percentage range of 0.5% or more to 30% or less. In other embodiments, particularly those embodiments for nitric oxide release, the wound dressing includes from 1.2 g or more to 29 g or less gas vesicles per kg hydrogel. In other embodiments, where a volume percentage basis is preferred, the wound dressing includes gas vesicles in a gas vesicle volume-percentage range of 1% or more to 20% or less. In yet other embodiments, particularly those embodiments for nitric oxide release, the wound dressing includes from 3.7 g or more to 13 g or less gas vesicles per kg hydrogel. In other embodiments, where a volume percentage basis is preferred, the wound dressing includes gas vesicles in a gas vesicle volume-percentage range of 3% or more to 10% or less.

Generally, wound dressing fabrics in accordance with this invention can contain any amount of gas vesicles that the fibers will hold. In some embodiments, particularly those embodiments for enhancing gas permeation, the wound dressing includes from 13 g or more to 150 g or less gas vesicles per kg "wet" dressing. The weight of "wet" dressing is evaluated when the fabrics or gauze is fully saturated with water. In other embodiments, particularly those embodiments for enhancing gas permeation, the wound dressing includes from 29 g or more to 105 g or less gas vesicles per kg wet dressing. In yet other embodiments, particularly those embodiments for enhancing gas permeation, the wound dressing includes from 48 g or more to 73 g or less gas vesicles per kg wet dressing.

In some embodiments, particularly those embodiments for nitric oxide release, the wound dressing includes from 0.6 g or more to 48 g or less gas vesicles per kg wet dressing. In other embodiments, particularly those embodiments for nitric oxide release, the wound dressing includes from 1.2 g or more to 29 g or less gas vesicles per kg wet dressing. In yet other embodiments, particularly those embodiments for nitric oxide release, the wound dressing includes from 3.7 g or more to 13 g or less gas vesicles per kg wet dressing.

In other embodiments, rhamnolipids are incorporated into the wound dressings. These biologics are essentially non-toxic (acute or chronic) and can be incorporated as ions or molecules dissolved in the aqueous solution inside a hydrogel, or as suspended oily droplets or solid aggregates.

Rhamnolipids (RLs) are glycolipid biosurfactants produced by microorganisms. They have antimicrobial activity against various bacteria (e.g. *Klebsiella pneumonia, Enterobacter aerogenes, Proteus mirabilis, Serratia marcescens, Salmonella thyphimurium, Alcaligenes faecalis, Citrobacter freundii, Pseudomonas aeruginosa, Escherichia coli, Bacillus cereus, Streptococcus faecalis, Bacillus subtilis, Staphylococcus aureus, Arthrobacter oxidans, Mycobacterium phlei, Micrococcus luteus, Staphylococcus epidermidis*, etc.) and fungi (e.g. *Alternaria* alternate, *Aspergillus niger, Gliocladium virens, Penicillium funiculosum, Botrytis cinerea, Rhizoctonia solani, Aureobasidium pullulans, Chaetomium globosum, Penicillium chrysogenum, Colletotrichum gloeosporioides, Fusarium solani, Trichoderma reesei*, etc.).

Rhamnolipids have a strong antifouling effect against bacterial attachment on surfaces. Rhamnolipids have also been shown to significantly improve healing of full-thickness burn wounds on rats, with accelerated wound closure (by 32% on Day 21) and decreased fibrous (47.5% lower collagen content in burn wounds).

Rhamnolipids have a positive effect on the rate of wound healing. Although this invention is not limited to or by the use of any specific concentration of rhamnolipids, the concentration and release rate are important factors. A higher concentration of rhamnolipids will result in better wound healing. Similarly, a higher release rate results in better wound healing. These parameters are easily adjustable in the wound dressing preparation by adjusting the amount loaded and the form of rhamnolipid used. Rhamnolipids in the ion or molecule form will be fast-releasing, while rhamnolipids in the water insoluble or lipid form will be slow-releasing. Methods of incorporation will be disclosed herein below.

Although virtually any rhamnolipids may be employed in accordance with this invention, in some embodiments the rhamnolipids are selected from one or two molecules of rhamnose linked to a β-hydroxyalcanoic acid or a chain of two β-hydroxyalcanoic acids joined by an ester bond. Two specific examples of rhamnolipids are rhamnosyl-β-hydroxydecanoyl-β-hydroxydecanoate (Rha-C10-C10), a mono-rhamnolipid; and rhamnosyl-rhamnosyl-β-hydroxydecanoyl-⊕-hydroxydecanoate (Rha-Rha-C10-C10), a di-rhamnolipid, which are found in fermentation broths. Several homolog molecules with other fatty-acid chains, differing in chain length and/or the extent of saturation, have been identified as rhamnolipids.

In one embodiment, the wound dressing in accordance with this invention includes from 10 mg or more to 10 g or less rhamnolipids, per kg hydrogel. In another embodiment, the wound dressing includes from 100 mg or more to 5 g or less rhamnolipids, per kg hydrogel. In yet another embodiment, the wound dressing hydrogel includes from 200 mg or more to 1 g or less rhamnolipids, per kg hydrogel.

In one embodiment, the wound dressing hydrogel includes 1 g or more rhamnolipids, in another embodiment, 5 g or more rhamnolipids, in yet another embodiment, 10 g or more rhamnolipids, and in other embodiments, 20 g or more rhamnolipids, per kg total weight of hydrogel.

In one embodiment, the wound dressing in accordance with this invention includes from 10 mg or more to 5 g or less rhamnolipids, per kg "wet" dressing. As described above, the weight of wet dressing is measured when fully saturated with water. In another embodiment, the wound dressing fabrics includes from 100 mg or more to 3 g or less rhamnolipids, per kg wet dressing. In yet another embodiment, the wound dressing fabrics includes from 200 mg or more to 1 g or less rhamnolipids, per kg wet dressing.

In one embodiment, the wound dressing fabric includes 1 g or more rhamnolipids, in another embodiment, 5 g or more rhamnolipids, in yet another embodiment, 10 g or more rhamnolipids, and in other embodiments, 20 g or more rhamnolipids, per kg total weight of wet dressing.

In yet another embodiment, the wound dressing contains sophorolipids. Sophorolipids (SLs) are another major group of glycolipid biosurfactant. Sophorolipids are good skin moisturizers, mildly antimicrobial, and enhance healthy skin cell growth (stimulated fibroblast metabolism and collagen neosynthesis, and fibrinolytic property).

Although virtually any sophorolipids may be employed in accordance with this invention, in some embodiments the sophorolipids are selected from those compounds consisting of a sophorose (a dimer of glucose) linked with a glycosidic bond to a terminal (ω) or subterminal (ω-1) hydroxyl fatty acid. Sophorolipids can have open (acidic) and closed (lactonic) structures. The hydroxyl fatty-acid moiety of lactonic sophorolipids forms a macrocyclic lactone ring with the 4″-OH group of the sophorose, while that of acidic ones remains a free acid. Sophorolipids can also vary in their extents of acetylation at the 6′- and 6″-OH groups (typically diacetylated) as well as the chain lengths of their fatty acids (usually $C_{16}$-$C_{18}$).

In one embodiment, the wound dressing includes 1 g or more to 20 g or less sophorolipids per kg hydrogel. In another embodiment, the wound dressing includes 5 g or more to 10 g or less sophorolipids per kg hydrogel. In one embodiment, the wound dressing hydrogel includes 1 g or more sophorolipids, in another embodiment, 5 g or more sophorolipids, in yet another embodiment, 10 g or more sophorolipids, and in other embodiments, 20 g or more sophorolipids, per kg total weight of hydrogel.

In one embodiment, the wound dressing fabric includes 1 g or more to 20 g or less sophorolipids per kg wet dressing. In another embodiment, the wound dressing fabric includes 5 g or more to 10 g or less sophorolipids per kg wet dressing. The weight of wet dressing is measured when fully saturated with water. In one embodiment, the wound dressing fabric includes 1 g or more sophorolipids, in another embodiment, 5 g or more sophorolipids, in yet another embodiment, 10 g or more sophorolipids, and in other embodiments, 20 g or more sophorolipids, per kg total weight of wet dressing.

Wound dressings described herein may optionally contain structural materials (such as polymers, pre-polymers, and monomers to be polymerized in situ) to provide suitable mechanical strength, water absorbency, and the often micro- or nano-scopically porous matrices; modifiers (such as organic polymers or monomers and inorganics), for modifying the physical/chemical properties; and crosslinking agents, (such as bivalent, multivalent and polymeric ions including, for example, calcium, ferrous iron, ferric iron, sulfate, phosphate, tetraborate, polyethyleneimine and other polyamines, oxalic acid, citric acid, tartaric acid and other polycarboxylic acids, polyamino carboxylic acids, and tripolyphosphate; and other reactive crosslinking compounds such as genipin, glutaraldehyde, formaldehyde, epoxy compound, and carbodiimide) for forming ionic or covalent bonds or other binding interactions with two and more entities (functional groups, compounds, aggregates, complexes, fibers, and other physical structures) in the wound dressing formulations, and, thus, providing physical strength, chemical stability, the adjustability and/or reversibility of hydrogel properties according or responding to pH, ionic strength, temperature, and/or other environmental conditions, and other beneficial effects for the applications of the wound dressings.

In some embodiments, the wound dressings of this invention contain two or more of gas vesicles, rhamnolipids, and sophorolipids. In other embodiments, the wound dressings contain all three of the gas vesicles, rhamnolipids, and sophorolipids components. In embodiments containing two or more of gas vesicles, rhamnolipids, and sophorolipids, the previously discussed amounts of each component can be used.

The wound dressing can be prepared as a single layer with gas vesicles, rhamnolipids and sophorolipids dispersed uniformly in the wound dressing. If desirable, the wound dressing can also be a two-layer wound dressing, with gas vesicles, rhamnolipids and sophorolipids only in the layer directly in contact with the wound site. The concentrations of gas vesicles, rhamnolipids and sophorolipids can be easily adjusted to best suit the wound type, size, and location. In embodiments containing gas vesicles, the gas vesicles can be evenly dispersed in the hydrogel or be embedded at high volume fractions in small, distributed cylinders that extend across the hydrogel. The latter form will have more effective gas permeation and require smaller amounts of gas vesicles.

The present invention broadly relates to a wound dressing have at least one layer of a wound dressing substrate having one or more of gas vesicles, rhamnolipids and sophorolipids. Wound dressings of the present invention can consist of any number of layers so long as at least one layer includes such a wound dressing substrate. In other embodiments, different layers can have different components selected from gas vesicles, rhamnolipids and sophorolipids. Some embodiments may have additional layers such as a barrier layer to prevent gas escaping to the ambient atmosphere from gas vesicles. Other embodiments can include a controlled-gas-diffusion layer to allow for better control of the rate of gas to the wound site. Other embodiments can include a concentrated-gas-vesicle layer to provide a higher level of a loaded gas to the wound site. Specific non-limiting examples are provided below, though it will be understood that the use of a singe layer or the combination of multiple layers and the selection of one or more of the gas vesicles, rhamnolipids and sophorolipids in one or more of those layers can take a multitude of forms.

Figure 1:
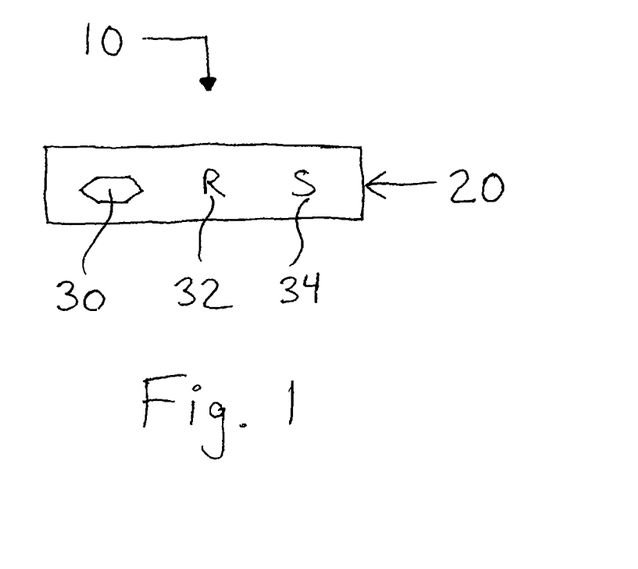
FIG. 1 is a schematic cross-sectional view of one embodiment of the present invention showing a wound dressing comprising rhamnolipids, sophorolipids, and gas vesicles.

In accordance with the preceding disclosures and with reference to FIG. 1, the present invention provides in a most basic form a wound dressing 10 comprising a substrate 20 including one or more of the following: gas vesicles 30, rhamnolipids 32 and sophorolipids 34. The various components are, obviously, selected as broadly as described above such that the substrate 20 may be a wound dressing fabric or a wound dressing polymer, and the gas vesicles 30 may be filled with ambient air or with any desired gas such as therapeutic oxygen or nitric oxide, and any combination of gas vesicles 30, rhamnolipids 32 and sophorolipids 34 may be incorporated into and/or on the substrate 20.

Figure 2:
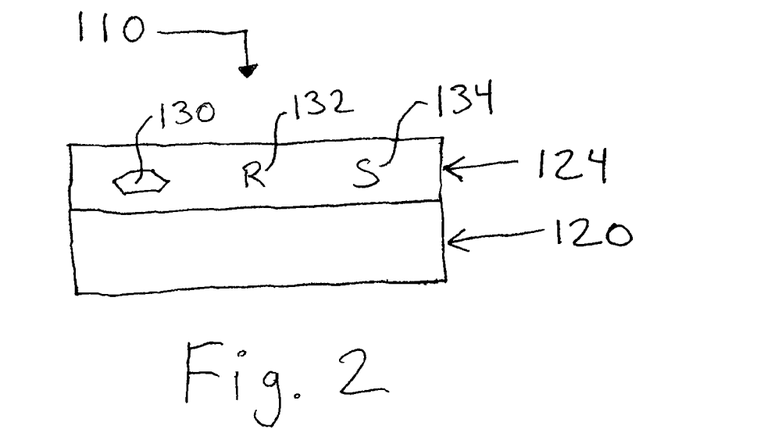
FIG. 2 is a schematic cross-sectional view of one embodiment of the present invention showing a wound dressing with multiple layers.

Another embodiment of this invention is shown in FIG. 2 and designated by the numeral 110, wherein like part to that of FIG. 1 receive like numerals though increased by 100. The wound dressing 110 includes a wound dressing substrate 120 that can be as broad as described with respect to wound dressing substrate 20 described above. This embodiment further includes an additional substrate 124 above wound dressing substrate 120, such that the wound dressing substrate 120 lies near the wound and the additional substrate 124 lays thereabove. In some such embodiments, the wound dressing substrate includes one or more of gas vesicles 130, rhamnolipids 132 or sophorolipids 134.

Figure 3:
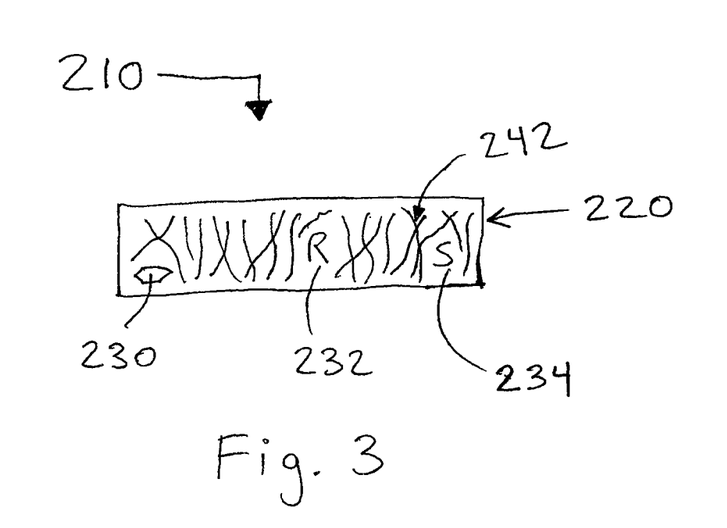
FIG. 3 is a schematic cross-sectional view of one embodiment of the present invention showing a wound dressing fabric.

In yet other embodiments, the wound dressings are provided with a plurality of fibers contained therein. With reference to FIG. 3, a wound dressing 210 includes a wound dressing substrate 220, having fibers 242 therein. Any combination of gas vesicles, rhamnolipids and sophorolipids may be incorporated into and/or on the substrate 220. Though fibers 242 could be provided to strengthen and shape a hydrogel, in some embodiments, the fibers 242 have gas vesicles embedded therein and/or attached on the fibers 242 surfaces. The gas vesicles may be filled with ambient air or with any desired gas such as therapeutic oxygen or nitric oxide. In embodiments where the fibers 242 are embedded with gas vesicles or have gas vesicles attached thereto, the substrate 220 may be devoid of gas vesicles 230, rhamnolipids 232 and sophorolipids 234. In other embodiments wherein the fibers 242 are embedded with gas vesicles or have gas vesicles attached thereto, the substrate 220 may also include any combination of gas vesicles 230, rhamnolipids 232 and sophorolipids 234 incorporated into and/or on the substrate 220. In embodiments where the fibers 242 include gas vesicles embedded therein and/or attached on the fibers 242 surfaces, the gas vesicles are forced into close proximity and thus gas transfer through the fibers proceeds quickly from one gas vesicle to the next.

Figure 4:
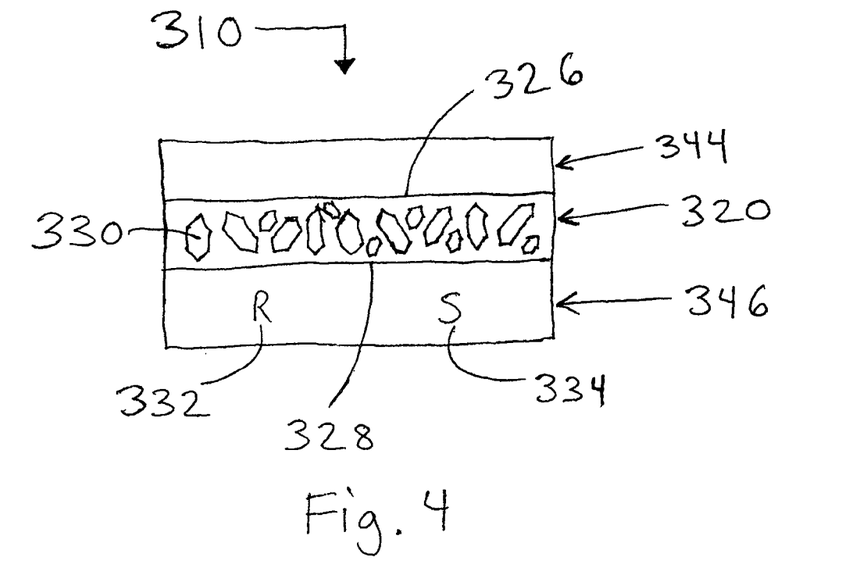
FIG. 4 is a schematic cross-sectional view of one embodiment of the present invention showing a wound dressing with multiple layers where the wound dressing has an optional layer of concentrated gas vesicles.

Another embodiment of this invention is shown in FIG. 4 and designated by the numeral 310 wherein a wound dressing 310 includes a wound dressing substrate 320, having a barrier layer 344 covering a first face 326 thereof, the barrier layer 344 serving to reduce, or entirely prevent, the transfer of gas, microbes, or other bodies through the barrier layer 344. The wound dressing 310 further includes an optional controlled-gas-diffusion substrate 346 that covers an opposed second face 328 of the wound dressing substrate 320. One embodiment contains gas vesicles 330 within the substrate 320. In these embodiments containing gas vesicles 330, the barrier layer 344 prevents dissipation of beneficial gases incorporated into gas vesicles 330 provided in the wound dressing substrate 320. Instead of dissipating through the barrier layer 344, the gas will diffuse through the controlled-gas-diffusion substrate 346 towards the direction of the wound bed. The controlled-gas-diffusion substrate 346 allows better for better control of the gas rate from the gas vesicles 330 to the wound bed. Upon reaching the wound bed, the gases can then impart their beneficial properties upon the wound. In some embodiments, the controlled-gas-diffusion substrate 346 optionally contains any combination of rhamnolipids 332 and sophorolipids 334.

In some embodiments where the wound dressing contains gas vesicles, a method for producing the wound dressing can include the steps of mixing a plurality of gas vesicles with a hydrogel polymer and crosslinking the hydrogel polymer to form a hydrogel.

In some embodiments where the wound dressing contains rhamnolipids, a method for producing the wound dressing can include the steps of preparing a wound dressing, partially drying the wound dressing, and placing the wound dressing in a solution comprising rhamnolipids such that the rhamnolipids will be absorbed into the wound dressing.

In some embodiments where the wound dressing contains sophorolipids, a method for producing the wound dressing can include the steps of preparing a wound dressing, partially drying the wound dressing, and placing the wound dressing in a solution comprising sophorolipids such that the sophorolipids will be absorbed into the wound dressing.

In some embodiments where the wound dressing contains gas vesicles, rhamnolipids, and sophorolipids, a method for producing the wound dressing can include the steps of mixing a plurality of gas vesicles with a polymer, crosslinking the polymer to form a hydrogel, preparing a wound dressing, partially drying the wound dressing, and placing the wound dressing in a solution comprising rhamnolipids and sophorolipids such that the rhamnolipids and sophorolipids will be absorbed into the wound dressing.

In embodiments of the present invention where the wound dressing is a hydrogel, the components (gas vesicles, rhamnolipids and sophorolipids), either alone or in various combinations, can be incorporated in the wound dressings either before or after the hydrogel polymers are crosslinked (or set) into the hydrogel structures (or matrices). To incorporate the gas vesicles, rhamnolipids or sophorolipids after crosslinking, they need to be smaller (in size) than the "pores" of the crosslinked hydrogel. Those skilled in the art are able to generally determine the pore size of the crosslinked hydrogel. This type of method is therefore more suitable for molecules but not suitable for larger entities.

On the other hand, while large and small components can all be incorporated in the wound dressings, higher fractions of the smaller components (particularly, the dissolved molecules) tend to be lost during the crosslinking procedure. The loss can be caused by the constriction/shrinking occurring with the crosslinking, which squeezes a portion of the liquid solution (carrying the dissolved or suspended small components) out of the hydrogel. The loss can also be caused by the diffusion of the small components from inside the hydrogel to the outside liquid used for crosslinking, for example, the calcium chloride solution used for crosslinking alginate-containing hydrogels. Therefore, incorporating the components before crosslinking is most suitable for larger, particularly not dissolved, components. In some embodiments, gas vesicles are incorporated as suspensions of individual vesicles before crosslinking resulting in a substantially homogeneous distribution.

The steps involved in the methods of incorporating the components before and after crosslinking are further discussed below. Each of the components (gas vesicles, rhamnolipids and sophorolipids) can be incorporated in different forms. Depending on the forms, different methods are chosen according to the following discussion for suitability.

In embodiments where the component(s) are incorporated before crosslinking, the first step is to dissolve and/or mix all hydrogel materials, including the hydrogel polymers and any desired special components (gas vesicles, rhamnolipids and/or sophorolipids), to form a solution or dispersion in a suitable solvent (often aqueous systems with or without pH buffer).

In some embodiments, low shear mixing is employed to avoid the incorporation of air bubbles into the solution. Low shear mixing is also helpful to avoid compromising the structure of the gas vesicles. If air bubble form, sonication or other agitation can be employed to remove the bubbles before crosslinking.

The hydrogel polymers, gas vesicles, rhamnolipids and sophorolipids have been previously disclosed. The suitable solvents will be well known to those of ordinary skill in the art for a given selection of on or more hydrogel polymers. Given the examples of hydrogel polymers previously provided, suitable solvents are selected from water, phosphate buffers or other buffers acceptable for use in wound dressings, aqueous solutions with low concentrations (<10% by weight) of ethanol, isopropanol, glycols, and other mild co-solvents with water.

Next, if desired, the solution or dispersion that has been prepared is poured into a mold. This optional step will give the final physical shape for the specifically intended application.

The solution or dispersion is then crosslinked (either physically or chemically). Where a mold is used, the solution or dispersion is crosslinked in the mold.

If necessary, any residual crosslinking agents or other hydrogel materials will then be removed. One means of removal by rinsing the residual material away.

In embodiments where the component(s) are incorporated after crosslinking, the first step is to dissolve and/or mix all the hydrogel materials, but excluding the component that is to be incorporated after crosslinking in a later step. A solution or dispersion will be formed in a suitable solvent where the solution is often an aqueous system that may include a pH buffer.

Next, if desired, the solution or dispersion that has been prepared is poured into a mold. This optional step will give the final physical shape for the specifically intended application.

The solution or dispersion is then crosslinked (either physically or chemically). Where a mold is used, the solution or dispersion is crosslinked in the mold.

If necessary, any residual crosslinking agents or other hydrogel materials will then be removed. One means of removal by rinsing the residual material away. This step can be omitted if the residual crosslinking agents or hydrogel materials do not interact with the solution used later in ways that will interfere with the intended loading of the desired component.

The prepared wound dressing piece is then placed in a solution containing a desired concentration of the component(s) to be incorporated. The component(s) will then be incorporated into the wound dressing by soaking or by passive diffusion.

If necessary, any residual crosslinking agents, other hydrogel materials, or remaining component(s) that is not incorporated into the hydrogel is then removed by rinsing or by other means.

Embodiments where the component(s) are incorporated after crosslinking can optionally include a step of partially dehydrating the wound dressing before the step of placing the wound dressing into a solution containing a desired concentration of the component(s) to be incorporated. In these embodiments, the wound dressing is first dehydrated to the desired extent so that when the dehydrated wound dressing is soaked in a solution containing a desired concentration of the component(s) to be incorporated, the wound dressing absorbs the component(s) more rapidly. This approach enhances the loading rate and completeness of loading.

In some embodiments, a portion of the desired component(s) can be incorporated before crosslinking while the remainder of the component(s) is loaded after crosslinking. These embodiments can be used to achieve a desired release pattern. For instance, the portion of the component(s) loaded after crosslinking can be in the form of dissolved molecules or ions that are released more rapidly from hydrogel (when applied to the wound) while the portion of the component(s) loaded before crosslinking can be in a less water soluble form, therefore being released at a slower and more regulated rate.

Optional ingredients, to the extent they are employed, can be added either before or after crosslinking.

In embodiments where the wound dressing is a hydrogel, it is generally preferred to use the method of loading gas-vesicle-containing fibers, calcium-rhamnolipid complex, and sophorolipid precipitates (as oily droplets or solids) before crosslinking, performing the crosslinking, then storing the wound dressing in sealed containers or packages with about 100 ml, per kg hydrogel, of an aqueous solution of about 100 mg/L rhamnolipids and about 1 g/L sophorolipids.

In embodiments where the wound dressing is a hydrogel including gas vesicles, it is generally preferred to use the method of loading the gas vesicles before crosslinking.

In embodiments where the wound dressing is a hydrogel including fibers embedded and/or surface modified with gas vesicles, it is generally preferred to use the method of loading the gas vesicle containing fibers before crosslinking.

In embodiments where the wound dressing is a hydrogel including rhamnolipids or sophorolipids, it is generally preferred to use the method of loading the rhamnolipids and sophorolipids both before and after crosslinking.

In embodiments where the wound dressing is a fabric, the preferred method is generally dependent on the fabric material. For fibers that are porous or that will swell and release small compounds, rhamnolipids and sophorolipids can be loaded inside the fibers, either as calcium-rhamnolipid complex and sophorolipid precipitate or as solutions. For non-porous, rigid fibers, calcium-rhamnolipid complex and sophorolipid precipitate should be trapped in the fiber matrix (outside individual fibers) during the mat formation process, or the already formed matrix needs to be soaked in a rhamnolipid/sophorolipid solution and then dried so that the biosurfactants adsorb and/or deposit onto the fiber surface.

In embodiments where the wound dressing is a fabric including gas vesicles, it is generally preferred to use the method of mixing the gas-vesicle-containing fibers with other non-gas-vesicle-containing fibers in the desired ratio before or during the matrix or mat forming process.

Rhamnolipids can have a pKa of about 5.5 to 5.9. They are soluble in water and present as negatively charged, proton-dissociated ions, at a pH higher than pKa. They are water insoluble when present as protonated, not charged acid form at low pH, or as complexes with multivalent metal ions such as calcium. Accordingly, rhamnolipids can be incorporated into the hydrogels as solutions of dissolved (small) rhamnolipid ions or as dispersions of (large) droplets or particles of either one of the two water insoluble forms.

Sophorolipids have two types: lactonic and acidic sophorolipids. Acidic sophorolipids, similar to rhamnolipids, have a fatty acid chain with a free carboxylic acid group at the end. In the lactonic sophorolipids, the carboxylic acid group forms an intra-molecular ester bond with a hydroxyl group in a sugar ring. Lactonic sophorolipids are therefore nonionic at all pH and their pH-independent solubility in aqueous systems is very poor. On the other hand, the water solubility of acidic sophorolipids, like rhamnolipids, is pH dependent; higher water solubility at higher pH. Accordingly, depending on the types (lactonic or acidic or mixture of the two), sophorolipids can also be incorporated in wound dressing either as solutions of dissolved (small) sophorolipid molecules or ions or as dispersions of (large) water-insoluble particles or droplets.

Incorporation of gas vesicles in wound dressings has special considerations, depending on the applications. Gas vesicles can be incorporated rather homogeneously as suspensions of individual vesicles before crosslinking. They are large structures that are generally not effectively incorporated after crosslinking. For effective enhancement of gas permeation (to allow $O_2$ in air to permeate rapidly to the wound covered by the dressing and to allow $CO_2$ produced by cells in the wound to escape rapidly through the dressing, to the outside air), gas vesicles should be in high concentrations, to minimize the far slower permeation through the liquid separation between the gas vesicles. If gas vesicles are incorporated as suspensions, the gas vesicle concentration should be high throughout the hydrogel. Alternatively, and more effectively, gas vesicles can be incorporated with high concentrations only locally, for example, with fibers embedded and/or surface-covered with high concentrations of gas vesicles, forming channels or paths for gas permeation across the hydrogel thickness. For controlled release of NO loaded in gas vesicles for antimicrobial activity, the gas vesicles can be first embedded in fibers or particles of denser (less permeable) hydrogel or non-hydrogel polymers, to control the release rate. For hydrogel-based wound dressings, the gas vesicles can also be added in an aqueous suspension. In these embodiments, the control of NO release rate relies more heavily on the hydrogel properties (such as polymer and modifier concentrations) and wound dressing design (such as being multilayered) and thickness. Furthermore, the NO permeation can be directed toward the wound and blocked/minimized toward the ambient. Thus, an embodiment including a wound dressing with a multilayered design can be used. The gas vesicle-containing fibers or particles, or the gas vesicles introduced in a concentrated suspension, can be incorporated in a hydrogel layer that is placed near the inner surface (to be in contact with the wound) and a denser hydrogel or even a largely impermeable coating in the outer layer (exposed to the ambient) can be utilized in the dressing design.

Wound dressings of the present invention possess beneficial properties over existing wound dressings. Some benefits include high antimicrobial activity, the ability to retain and absorb moisture, and improved gas permeation.

Embodiments of the present invention where the wound dressing contains rhamnolipids or sophorolipids have improved antimicrobial activity. Rhamnolipids and sophorolipids possess high antimicrobial activity and impart this advantage to the wound dressing.

Embodiments of the present invention where the wound dressing is hydrogel-based have improved ability to retain and absorb moisture. Hydrogels are highly absorbent materials and impart these properties to the wound dressing.

Embodiments of the present invention where the wound dressings contains gas vesicles also have improved ability to retain moisture based on limiting water vaporization and evaporation from the wound site. Conventional fiber wound dressings contain air space that aid in improving gas transfer through the wound dressing. However, these air spaces also allow water evaporation from the wound site. Embodiments of the present invention where the wound dressings contain gas vesicles result in a lower water evaporation rate from the wound site while also having improved gas transfer.

Embodiments of the present invention where the wound dressing contains gas vesicles have improved gas permeation properties. Embodiments of the present invention have differing gas permeation enhancement based on differing preparations and gas vesicle contents.

In embodiments where the gas vesicles are loaded with a gas, the gas vesicles and wound dressings are better able to controllably release the gaseous molecules. Embodiments of the present invention where the wound dressing has evenly distributed gas vesicles or gas-vesicle-containing fibers or particles, can also be more effective and easy to manufacture.

Embodiments of the present invention containing gas vesicles that are loaded with oxygen have improved properties of better facilitating of neovascularization, improved collagen synthesis, and the ability to prevent or minimize microbial infection.

Embodiments of the present invention containing gas vesicles that are loaded with nitric oxide have broad-spectrum antimicrobial activities and are able to promote angiogenesis by stimulating synthesis of vascular endothelial growth factor (VEGF) and fibroblast collagen.

Embodiments of the present invention can be designed in order to provide sustained gas release from the wound dressings. These wound dressings contain multiple layers of gas vesicles. In some embodiments, the layer closest to the wound has the lowest gas vesicle concentration, the next closest layer to the wound has a higher gas vesicle concentration, and so on. This arrangement allows more steady gas concentration during the clinical period.

In light of the foregoing, it should be appreciated that the present invention significantly advances the art by providing an improved wound dressing. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

Example 1

Steps of Making a Hydrogel Matrix that can Support the Incorporation of Rhamnolipids, Sophorolipids and Gas Vesicles to be Used as a Wound Dressing A gelatin-alginate based hydrogel matrix is made in this example. A 50 g/L solution of gelatin was first made by dissolving 2.5 g gelatin in 50 ml water at 60° C. in a covered beaker, under stirring at 300 rpm by a magnetic stir. The dissolution took about 10 minutes to ensure formation of a visually homogenous solution. The gelatin solution was then poured into a 100 ml stainless steel Waring blender container. Sodium alginate, totally 2.5 g, was then added in multiple small batches to the gelatin solution. After each addition of a small amount of alginate, the blender was turned on briefly (5-20 seconds) to help mix and dissolve alginate into the gelatin solution. Alginate needed to be added slowly to prevent chunk formation. Thus, prepared viscous solution with equal concentrations of gelatin and alginate had many trapped bubbles. The Waring blender container with the solution was sonicated for 1 hour at 60° C. in a sonicator water bath, to remove a majority of the bubbles. The sonicated hydrogel paste was then loaded in multiple 3 ml syringes. The syringes were placed vertically in the sonicator water bath and sonicated for another 1 hour at 60° C. to ensure removal of remaining fine bubbles. The degassed hydrogel in each syringe was then added to a petri dish (about 50 mm in diameter) and left to cool to room temperature. The cooled hydrogel was ready for crosslinking or other procedures used for loading gas vesicles, rhamnolipids and/or sophorolipids.

Example 2

Loading Rhamnolipids and Sophorolipids as a Solution

In this example, the gelatin-alginate hydrogel was made to contain 100 mg/L rhamnolipids and 60 g/L sophorolipids prior to the crosslinking. A biosurfactant solution of 5 g/L rhamnolipids and 3 g/L sophorolipids was prepared in a pH 7 phosphate buffer. (At this pH, rhamnolipids are soluble at high concentrations but typical sophorolipid mixtures, with mostly lactonic sophorolipids, are soluble only at concentrations lower than 5 g/L, depending on exact composition of the sophorolipid mixture.) 1 mL of the solution was added to the Waring blender container after all the alginate (2.5 g) had been added and dissolved to make the gelatin-alginate solution, as described in Example 1. After addition of the rhamnolipid-sophorolipid solution, the Waring blender was turned on for about 3-5 seconds. The biosurfactants would cause trapping of much more fine bubbles. Too much mixing at this stage should be avoided. The Waring blender container with the gelatin-alginate-rhamnolipid-sophorolipid solution was then sonicated, followed by the same remaining procedures as described in Example 1.

Example 3

Loading of Rhamnolipids as Calcium Rhamnolipid Complex

Calcium rhamnolipid complex was first prepared as follows: 0.1 ml of an 80 g/L rhamnolipid solution was added into a centrifuge tube containing 1 ml of a 0.1 M (11.1 g/L) calcium chloride solution. The cationic calcium ions would complex with anionic rhamnolipids to form insoluble precipitates. The calcium-rhamnolipid complex was collected by centrifugation. In earlier experiments, the complexation was found to be almost complete, with undetectable rhamnolipids (by standard anthrone analysis) in the supernatant collected from the centrifugation.

The gelatin-alginate solution, not yet sonicated for removal of bubbles, was prepared in the Waring blender container as described in Example 1. The collected calcium-rhamnolipid complex was added to the Waring blender container and mixed for about 3-5 seconds. As described in Example 2, too much mixing at this stage tended to trap excessive amounts of fine bubbles. The subsequent steps were the same as those described in Example 1. Although not measured, the cooled hydrogel prepared in this example was expected to contain about 180 mg/L rhamnolipids prior to crosslinking.

Example 4

Preparation of Fibers with Embedded Gas Vesicles 0.25 grams of sodium alginate powders were slowly added to a tube of 5 ml suspension of 0.4 g/L gas vesicles. The alginate powders were added in multiple, small batches and the suspension was gently stirred with a spatula for dissolution of alginate. Gentle, low shear mixing is necessary to prevent collapse of gas vesicles and trapping of fine bubbles. The prepared gas vesicle-alginate mixture was loaded in a 5 ml syringe. The syringe outlet was then attached to one end of a silicone tubing. A stainless steel syringe needle was attached to the other end of the tubing. Then, the syringe was placed on a syringe pump and the needle was held half-submerged in a rectangular coagulation bath containing a 20 g/L calcium chloride solution at room temperature. The syringe pump was turned on to push out the gas vesicle-alginate mixture at a rate of 5 ml/h. The mixture, once pushed out of the needle, solidified almost instantaneously due to the crosslinking of alginate by calcium ions that rapidly penetrate the thin cylinder of porous hydrogel mixture. As soon as a small amount of the solidified mixture was formed at the tip of the needle, a pair of tweezers was used to slowly pull the mixture, as it was pumped out of the needle tip. The pulled mixture formed into an initial length of fiber crosslinked by the calcium chloride solution. This initial length of fiber was drawn under two submerged, stationary rods placed horizontally in the coagulation bath and then wound on a roller outside the coagulation bath. The roller was rotated at a slow speed to continuously pull the pumped mixture through the crosslinking solution and collect the crosslinked fiber onto the roller.

Example 5

Loading of Gas Vesicle-Containing Fibers in a Gelatin-Alginate Hydrogel Prior to Crosslinking A hydrogel of 30 g/L gelatin and 20 g/L sodium alginate was prepared, by a similar procedure as that described in Example 1. The lower polymer (gelatin and alginate) concentration, i.e., totally 50 g/L as compared to the 100 g/L used in Example 1, made the hydrogel less viscous and can be mixed by gentler magnetic stirring. The use of Waring blender for dissolving alginate was not necessary. The dissolved hydrogel was sonicated at 60° C. for 1 h to remove the bubbles. (This step was also not necessary if the mixing was done by gentle mixing without trapping fine bubbles.) After the degassed hydrogel was cooled in a beaker with gentle mixing to 30-40° C., the gas vesicle-containing fibers were added and gently mixed for dispersion of the fibers in the hydrogel. Prepared gas vesicle-gelatin-alginate mixture was then dispensed to petri dishes and cooled to room temperature.

Example 6

Crosslinking of Hydrogel

Different methods can be applied for the crosslinking purpose. Glutaraldehyde is one of the common methods used to chemically crosslink protein-based materials such as gelatin and soy proteins. Calcium chloride solution is commonly used for crosslinking alginate.

For crosslinking the concentration of glutaraldehyde can be varied from 1 to 50 g/L. Unfortunately, glutaraldehyde can have negative effects to skin cells. Although the negative effects can be minimized by using the lowest glutaraldehyde concentration that gives acceptable crosslinking effect for the particular system and application and by washing the hydrogels after crosslinking to remove residual glutaraldehyde, the preferred example was to crosslink the alginate by calcium ions.

For alginate crosslinking by calcium ions, the concentration of calcium chloride solution can be in the range of 1 to 100 g/L. The favorable concentration range is from 10 to 50 g/L. The most preferred concentration is in the range of 20 to 30 g/L. Moreover, the duration of cross linking is important. It can be varied from 2 minutes to 1 day, depending on the calcium chloride concentration and the thickness/diameter of the materials that need to be penetrated by the calcium ions for crosslinking. The more suitable duration is in the range of 30 minutes to 15 hours.

The cooled hydrogel pieces in petri dishes, as prepared by the methods described previously, were all crosslinked for 2 hours in 6 ml of a 20 g/L calcium chloride solution added to each of the petri dish containing the hydrogel piece. The crosslinked hydrogel was then rinsed with deionized water to remove excess calcium ions.

Example 7

Loading of Rhamnolipids by Soaking the Crosslinked Hydrogel in a Rhamnolipid Solution The hydrogel prepared in Example 1 and crosslinked by the calcium chloride solution as described in Example 5 was soaked in 6 mL of a 200 mg/L rhamnolipid solution for 48 hours. Rhamnolipids diffused into the hydrogel due to the concentration gradient.

Example 8

Effects of Hydrogel Polymer Composition

Five hydrogel samples were prepared according to the method described in Example 1 but with different hydrogel polymer concentrations: 100 g/L gelatin and 10 g/L sodium alginate; 50 g/L gelatin and 10 g/L sodium alginate; 50 g/L gelatin and 50 g/L sodium alginate; 10 g/L gelatin and 50 g/L sodium alginate; and 10 g/L gelatin and 100 g/L sodium alginate.

The hydrogel samples were crosslinked by a 50 g/L calcium chloride solution according to the method described in Example 6. The mechanical strength was not measured. It was clear from sample handling (such as transferring the sample from one petri dish to another) that the crosslinked samples with higher alginate concentrations were physically harder and that the gelatin concentration did not affect the mechanical strength significantly.

Figure 5:
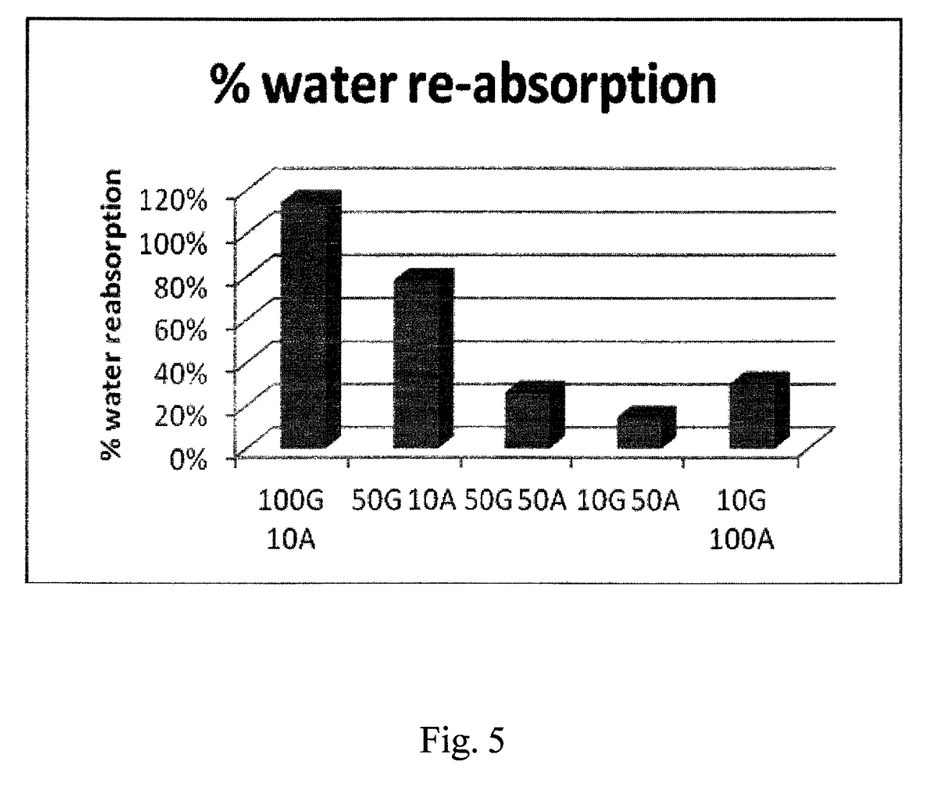
FIG. 5 is a graph showing values for percent water re-absorption of specific embodiments of the present invention.

The weight of each crosslinked hydrogel sample was recorded. The hydrogel samples were then dried at room temperature (for up to 96 h) and weighed daily, to reach constant weights. 3 mL of water was then added to each petri dish containing a piece of dried hydrogel. The hydrogel was allowed to absorb the added water for 24 h. The weight of each re-hydrated hydrogel sample was weighed. The weight of absorbed water was calculated and then divided by the weight of water present in the original hydrogel before drying. The calculated value was considered as an indicator of the reversibility of water absorption of the hydrogel through dehydration-rehydration cycle. The obtained values for % water re-absorption are shown in FIG. 5. Water reabsorption was good in hydrogels with 10 g/L alginate but very poor (<30%) in hydrogels with 50 g/L or 100 g/L alginate. If rhamnolipids and/or sophorolipids are to be loaded by soaking dried hydrogels in solutions of these biosurfactants, the alginate concentration needs to be controlled at lower than 50 g/L. At a similar alginate concentration (either 10 g/L or 50 g/L in the tested samples), a higher gelatin concentration moderately improved the water reabsorption.

Example 9

Attaching Gas Vesicles onto Wall of Polymer Fibers to Form Efficient Paths for Gas Permeation, as an Alternative Method to Entrapping Gas Vesicles Inside the Fibers A: Preparation of Poly(Methyl Methacrylate) (PMMA) Fibers Poly(methyl methacrylate), commonly abbreviated as PMMA, is a transparent non-hydrogel thermoplastic. 2 g PMMA was melted in a 25 mL beaker using a hot plate at above 160° C. After the polymer was melted, the tip of a pair of tweezers or a glass stick was inserted into the polymer melt and, as the tweezers or glass stick was slowly lifted, a thin long fiber was easily drawn out of the melted polymer. The fiber diameter drawn in this example was about 150-200 micrometers. The diameter could be changed to some extent by the speed of fiber-drawing; thinner at faster speeds and thicker at slower speeds. The fiber was naturally and rapidly hardened as it was air-cooled once being drawn out of the hot polymer melt.

B: Acid Catalyzed Hydrolysis to Create Carboxylic Acid Groups on the PMMA Fiber Surface About 0.2 g of the PMMA fibers prepared above was submerged in a beaker of 50% 2-propanol aqueous solution and sonicated for 10 minutes. Then, the fibers were removed using a pair of tweezers and dried under a gas stream of nitrogen. After drying, the PMMA fibers were submerged in 3M sulfuric acid at 60° C. for 20 minutes to hydrolyze the methyl ester bonds on the fiber surface (shown by the following scheme). The surface-modified PMMA fibers were removed from the sulfuric acid solution, rinsed with large amount of deionized water, then rinsed with 2-propanol, and finally dried again under a nitrogen stream.

C: Attachment of Gas Vesicles onto the Surface-Modified PMMA Fibers

Bottles of 1-ethyl-3-[3-dimethylaminopropyl]carbodiimide hydrochloride (EDC) and N-hydroxysuccinimide (NHS) were removed from refrigerator and equilibrated to room temperature prior to use. 0.4 mg of EDC and 0.6 mg of NHS were added to a tube containing 3 ml pH 5 phosphate buffer and 0.01 g of the surface-modified PMMA fibers. The content in the tube was allowed to react for 15 minutes at room temperature before 1.4 µL of 2-mercaptoethanol were added to quench the reaction. As shown by the following reaction scheme, EDC reacted with a carboxyl group on the surface-modified PMMA fibers to form an amine-reactive O-acylisourea intermediate. This intermediate was not very stable. NHS reacted with this intermediate to form a more stable amine-reactive ester.

Figure 6:
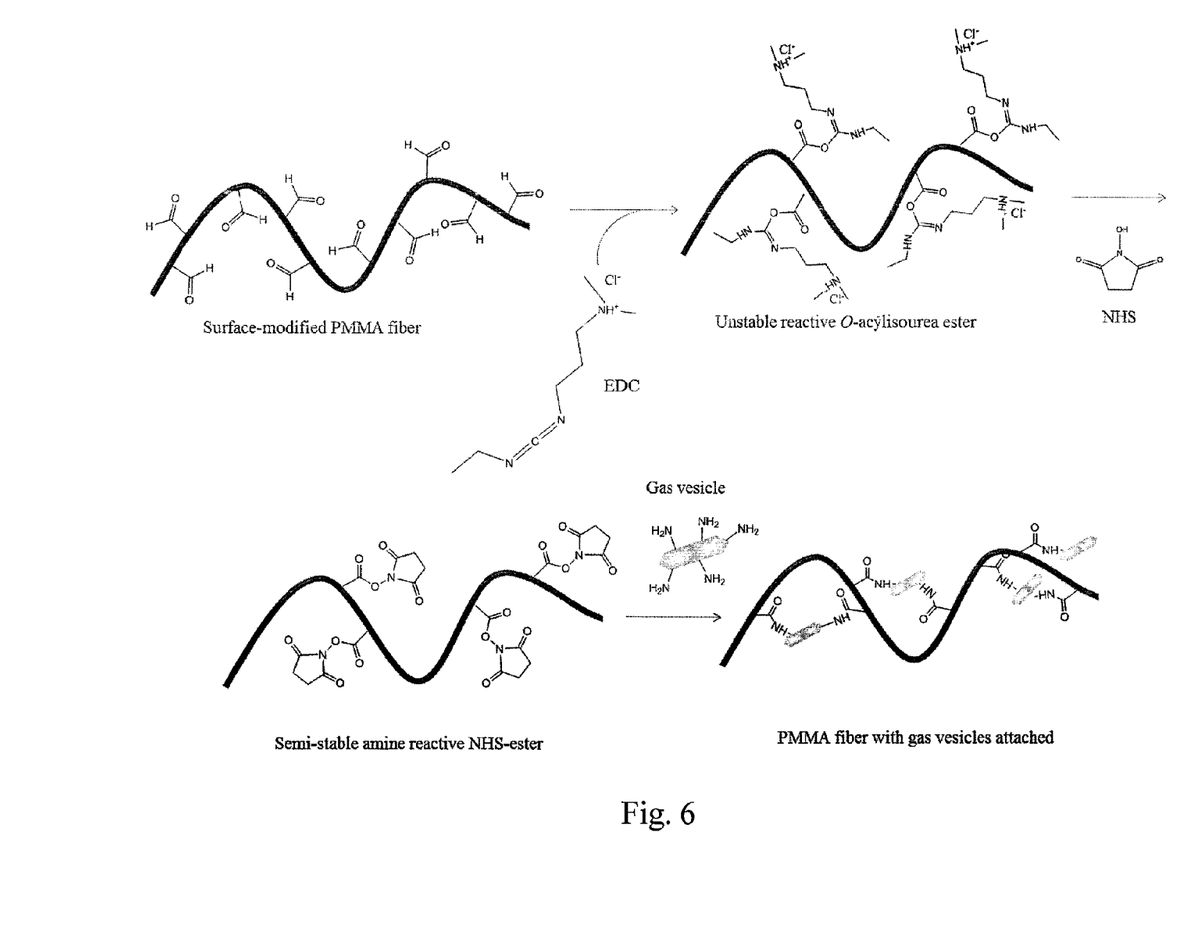
FIG. 6 is a reaction schematic involving 1-ethyl-3-[3-dimethylaminopropyl]carbodiimide hydrochloride (EDC) and N-hydroxysuccinimide (NHS) that was used to prepare specific embodiments of the present invention.

By the reactions with EDC and NHS as shown in FIG. 6, the carboxyl groups on the surface of modified PMMA fibers were converted into the amine-reactive ester groups. These surface-activated fibers were next moved to 3 ml pH 7 phosphate buffer containing 0.2 g/L gas vesicles. The protein wall of gas vesicles, containing many reactive amine groups, would react with the EDC and NHS activated ester groups on the fiber surface to form multiple amide bonds, causing the gas vesicles to attach to the fiber surface by these covalent bonds. This reaction between gas vesicles and activated fibers was allowed to proceed for 2 hours at room temperature. The PMMA fibers, with gas vesicles covering the fiber surface, were gently rinsed with deionized water and then stored in a refrigerated pH 7 phosphate buffer. The surface coverage of fiber by gas vesicles was observed and confirmed with an atomic force microscope.

Example 10

Loading of Gas Vesicles in a Gelatin-Alginate Hydrogel Prior to Crosslinking A hydrogel of 30 g/L gelatin and 20 g/L sodium alginate was prepared, by a similar procedure as that described in Example 1. The lower polymer (gelatin and alginate) concentration, i.e., totally 50 g/L as compared to the 100 g/L used in Example 1, made the hydrogel less viscous and can be mixed by gentler magnetic stirring. The use of Waring blender for dissolving alginate was not necessary. The dissolved hydrogel was sonicated at 60° C. for 1 h to remove the bubbles. (This step was also not necessary if the mixing was done by gentle mixing without trapping fine bubbles.) After the degassed hydrogel was cooled in a beaker with gentle mixing to 30-40° C., the gas vesicles were added and gently mixed for dispersion of the gas vesicles in the hydrogel. Prepared gas vesicle-gelatin-alginate mixture was then dispensed to petri dishes and cooled to room temperature.

Various modifications and alterations that do not depart from the scope and spirit of this invention will become apparent to those skilled in the art. This invention is not to be duly limited to the illustrative embodiments set forth herein.

What is claimed is:

1. A wound dressing for dressing a wound comprising a wound dressing substrate including gas vesicles, where the wound dressing substrate is selected from the group consisting of fabrics, hydrogels, solid films, porous foams, porous membranes, creams, meshes, and gauzes, the wound dressing substrate further comprising rhamnolipids.

2. The wound dressing of claim 1, the wound dressing substrate comprising rhamnolipids and sophorolipids.

3. A method for producing the wound dressing of claim 2, the method comprising the steps of:
   preparing a plurality of fibers;
   preparing a fabric wound dressing substrate from the plurality of fibers; and
   incorporating gas vesicles and rhamnolipids and sophorolipids in the fabric wound dressing substrate.

4. The method of claim 3, wherein, in said steps of preparing, said fibers include gas vesicles embedded in or incorporated on or both embedded in and incorporated on the plurality of fibers, such that the gas vesicles are incorporated into the fabric wound dressing substrate upon said step of preparing the fabric wound dressing substrate.

5. The method of claim 3, wherein said step of incorporating occurs after said step of preparing a fabric wound dressing and includes placing the fabric wound dressing substrate in a solution comprising gas vesicles, and optionally, one or more of rhamnolipids, and sophorolipids, such that the gas vesicles, and optionally, one or more of rhamnolipids, and sophorolipids, are absorbed into the fabric wound dressing.

6. The wound dressing of claim 2, wherein the wound dressing substrate includes fibers, said fibers being selected from fibers having said gas vesicles attached thereto and fibers that are embedded with said gas vesicles.

7. A method for producing a wound dressing for dressing a wound comprising the steps of:
   preparing a hydrogel polymer solution comprising a hydrogel polymer;
   crosslinking the hydrogel polymer to form a hydrogel wound dressing substrate; and
   incorporating gas vesicles in the hydrogel wound dressing substrate,
   incorporating one or more of rhamnolipids and sophorolipids in the hydrogel wound dressing substrate, wherein the hydrogel polymer solution includes gas vesicles, and optionally, one or more of rhamnolipids, and sophorolipids, such that the gas vesicles, and optionally, one or more of rhamnolipids, and sophorolipids, are incorporated into the wound dressing substrate upon crosslinking of the hydrogel polymer.

8. A wound dressing comprising a wound dressing substrate including gas vesicles, wherein the wound dressing substrate includes fibers, said fibers being selected from fibers having said gas vesicles attached thereto and fibers that are embedded with said gas vesicles.

9. The wound dressing of claim 8, wherein the wound dressing substrate includes fibers that are embedded with gas vesicles.

10. The wound dressing of claim 8, wherein the wound dressing substrate includes fibers having gas vesicles attached thereto.

11. A wound dressing for dressing a wound comprising a wound dressing substrate including gas vesicles, where the wound dressing substrate is selected from the group consisting of fabrics, hydrogels, solid films, porous foams, porous membranes, creams, meshes, and gauzes, the wound dressing substrate further comprising sophorolipids.

* * * * *